United States Patent [19]

Suzuki

[11] Patent Number: 4,747,685
[45] Date of Patent: May 31, 1988

[54] BIOLOGICAL MICROPARTICLE INSPECTION APPARATUS

[75] Inventor: Yoshinori Suzuki, Yokohama, Japan

[73] Assignee: Kabushiki Kaisha Toshiba, Kawasaki, Japan

[21] Appl. No.: 841,817

[22] Filed: Mar. 20, 1986

[30] Foreign Application Priority Data

Mar. 29, 1985 [JP] Japan ................................. 60-66049

[51] Int. Cl.$^4$ ...................... G01N 1/10; G01N 33/487; G01N 15/12; G01N 15/14
[52] U.S. Cl. ..................................... 356/36; 356/336; 356/341; 377/11; 377/12
[58] Field of Search ................ 250/574; 356/336, 341, 356/343, 36, 39; 377/10, 11, 12

[56] References Cited

U.S. PATENT DOCUMENTS

| 3,977,995 | 8/1976 | Louderback et al. | 356/39 X |
| 4,078,863 | 3/1978 | Eriksson et al. | 356/336 X |
| 4,174,952 | 11/1979 | Cannell et al. | 250/574 X |
| 4,348,107 | 9/1982 | Leif | 356/73 X |

FOREIGN PATENT DOCUMENTS

| 20064230 | 10/1982 | European Pat. Off. |
| 20121262 | 10/1984 | European Pat. Off. |
| 20121261 | 10/1984 | European Pat. Off. |
| 1232705 | 5/1971 | United Kingdom |
| 2009410 | 6/1979 | United Kingdom |

OTHER PUBLICATIONS

The Review of Scientific Instruments, vol. 43, No. 3, pp. 404-409, "Fluorescence Activated Cell Sorting"; W. A. Bonner et al., Mar. 1972.
The Review of Scientific Instruments, vol. 44, No. 9, pp. 1301-1310, "A New Multiparameter Separator for Microscopic Particles and Biological Cells"; J. A. Steinkamp et al., Sep. 1973.

Primary Examiner—Vincent P. McGraw
Attorney, Agent, or Firm—Oblon, Fisher, Spivak, McClelland & Maier

[57] ABSTRACT

A biological microparticle inspection apparatus has a reactor in which blood containing T cells is mixed with latex-labeled antibodies and T cells are coupled with the antibodies to form complexes. A particle size measurement unit is provided for measuring the size of the particles contained in the blood, including the complexes. A signal processing unit processes the measured sizes of the particles outputting signals only when the measured sizes fall within a range of the size of the complex, and counts the number of the output signals. The number of the output signals corresponds to the number of the complexes and hence the T cells.

10 Claims, 7 Drawing Sheets

BIOLOGICAL MICROPARTICLE INSPECTION APPARATUS

BACKGROUND OF THE INVENTION

1. Field of the Invention

The present invention relates to a biological microparticle inspection apparatus for selectively counting specified biological microparticles such as blood corpuscles or cells of biological tissues.

2. Description of the Prior Art

Selective counting of specified biological microparticles such as blood corpuscles or the cells of a biological tissue is very important for assessing the state of the biological entity, especially a diseased state. For example, inflammation or allergy can be correctly diagnosed by selectively counting neutrophils, basophils, and eosinophils among granulocytes, or by selectively counting T or B cells of lymphocytes.

Selective counting of specified blood corpuscles is performed by a medical technician who discriminates stained blood corpuscles and counts them with an eye under a microscopic observation. However, in this method, since the technician discriminates and counts the stained corpuscles one at a time, processing takes a long period of time and is very inefficient.

Another method exists which involves staining blood corpuscles to prepare a specimen. The specimen is screened on by a TV camera through a microscope. Then, the stained blood corpuscles are discriminated and counted by means of a pattern recognition technique. However, with this method, the preparation of the stained specimen is complicated and time-consuming. In addition, many errors frequently occur in stained blood corpuscle discrimination, and the stained corpuscles cannot be counted with accuracy.

According to still another recently proposed method, an antibody specific to the type of blood corpuscle to be counted is labeled with a fluorescent material. The labeled antibody is mixed with blood, and the corpuscles which are coupled with the labeled antibody are counted. However, with this method, the amount of fluorescent light emitted from blood corpuscles coupled with labeled antibodies is very small. In order to measure such weak fluorescence, an Ar laser or the like of about 1 W or more must be used as a high-intensity light source. The use of the high-intensity light source renders the apparatus bulky and expensive. Further, the measurement of the desired fluorescent light is influenced by the presence of natural fluorescent light emitted by proteins or fats floating in the blood.

SUMMARY OF THE INVENTION

It is an object of the present invention to provide a biological microparticle inspection apparatus which can selectively count specified biological microparticles with high precision and speed.

According to the present invention, there is provided a biological microparticle inspection apparatus comprising: a first means for mixing coupling bodies capable of coupling specifically with specified biological microparticles and labeled with particles having substantially the same size, together with a sample containing biological microparticles including said specified biological microparticles, thereby coupling said labeled coupling bodies with said specified biological microparticles to form complexes, and a second means for selectively counting the number of said complexes.

According to the present invention the particle size of specified microparticles to be measured can be changed by coupling with the labeled coupling body to form the complexes. Therefore, the number of the specified particles can be measured by using a particle size measurement unit of scattered light type or of Coulter type. In the former type of unit, the size of the particles is measured by measuring the amount of forward scattered light or forward/side scattered light. In the latter type of unit, the size of the particles is measured by measuring electrical resistance. Particles having a size of the complexes can be discriminated and the number of the complexes and hence the specified microparticles can be selectively counted.

The blood corpuscles such as neutrophils, eosinophils, basophils, monocytes, T cells, or B cells having different characteristics can be differentiated by allowing them to be coupled with the labeled coupling bodies which have specificity to respective types of microparticles.

DETAILED DESCRIPTION OF THE PREFERRED EMBODIMENTS

Figure 1:
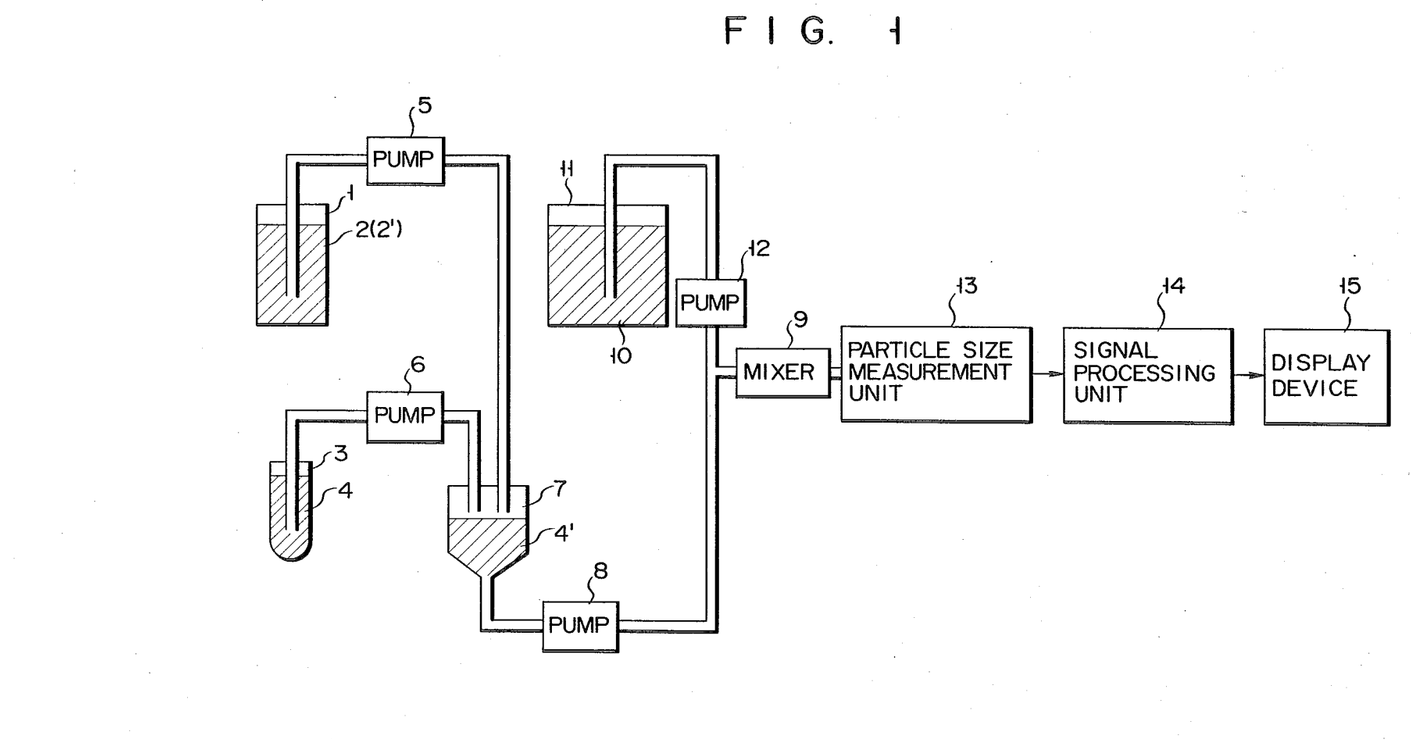
FIG. 1 is a schematic diagram showing the configuration of the apparatus according to a first embodiment of the present invention.

FIG. 1 shows a schematic configuration of the apparatus according to a first embodiment of the present invention. A reagent tank 1 contains a latex-labeled antibody reagent 2. The reagent 2 is obtained by labeling an antibody having specificity to T cells with latex having a uniform particle size of about 19.8 $\mu$m. The labeling can be effected by a method known per se. A test tube 3 contains blood 4, which includes T cells to be measured. The reagent 2 and the blood 4 are supplied to a reactor 7 (first means) by pumps 5 and 6, respectively. In the reactor 7 the reagent 2 and the blood 4 are mixed to form complexes. In order to permit an easy antigen-antibody reaction, the reactor 7 is kept at about 37° C.

Blood 4', sufficiently reacted with the latex-labeled antibody reagent 2 in the reactor 7, is supplied to a mixer 9 by a pump 8. A diluting solution (e.g., phosphate buffered saline) 10 is supplied from a tank 11 to the mixer 9 by a pump 12. The mixer 9 mixes the blood 4' with the diluting solution 10 to prepare dilute blood.

A predetermined amount of the dilute blood is passed through a particle size measurement unit 13 which measures the size of each of the particles present in the dilute blood, including T cells coupled with the latex-labeled antibody. The blood 4' is diluted with the diluting solution 10 so that two or more blood corpuscles are not counted as one corpuscle. The detected result is supplied to a signal processing unit 14. The unit 14 then calculates the number of T cells which are coupled with the latex-labeled antibody. The latexes used herein can be those of polyvinyl toluene or polystyrene spheres, which are available from The Dow Chemical Company.

A display device 15, which comprises, e.g., a cathode ray tube, displays a histogram of the detected results. As variables, forward scattered light intensity or electrical resistance of the particles is plotted along the abscissa axis, and the number of the particles is plotted along the ordinate axis.

The particle size measurement unit 13 comprises either a forward scattered light detection unit and a flow cell having an orifice of a transparent material such as glass, or an electrical resistance detection unit and such a flow cell. When particles flowing into the orifice of the flow cell are irradiated with light, scattered light is generated. The intensity of forward scattered light is proportional to the particle size. T cells which have coupled with the latex-labeled antibody and increased in size can be discriminated from other sample particles and counted on the basis of the above principle. Alternatively, T cells which have coupled with the latex-labeled antibody and increased in size can be discriminated from other sample particles and counted on the basis of measurement of the electrical resistance of particles before and after the particles enter the orifice, since the electrical resistance increases in proportion to the particle size.

Figure 2A:
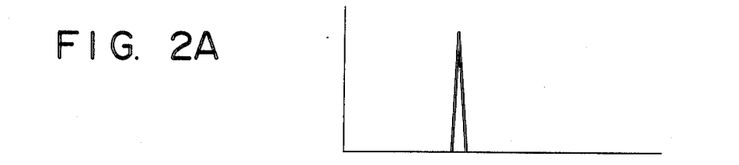
FIGS. 2A, 2B, 2C and 2D, and FIGS. 3A, 3B and 3C show histograms obtained in the first embodiment of the present invention.
Figure 2B:
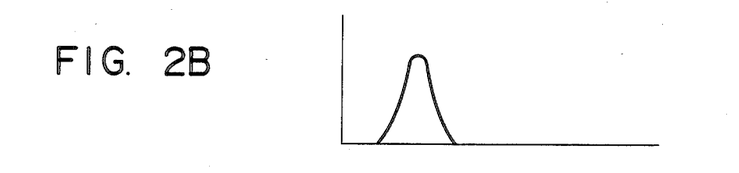
Figure 2C:
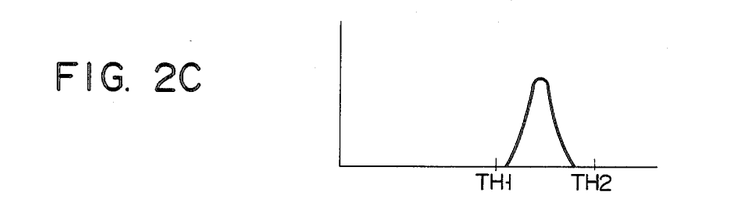

When the latex-labeled antibody, blood corpuscles, and T cells coupled with the latex-labeled antibody are detected, different intensities of forward scattered light or different electrical resistances are displayed as indicated by the histograms in FIGS. 2A, 2B and 2C. FIG. 2A shows a histogram of the latex-labeled antibody, FIG. 2B shows a histogram of blood corpuscles, and FIG. 2C shows a histogram of T cells coupled with the latex-labeled antibody. When particles having a forward scattered light intensity or electrical resistance falling within a range between thresholds TH1 and TH2, indicated in FIG. 2C, are counted, the number of T cells coupled with the latex-labeled antibody can be determined.

Figure 2D:
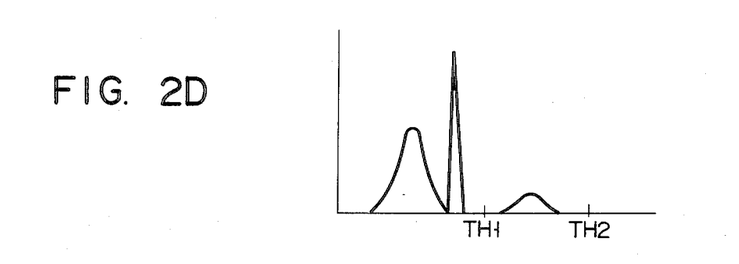

In practice, the display device 15 displays a histogram of blood corpuscles, a histogram of the latex-labeled antibody, and a histogram of T cells coupled to the latex-labeled antibody, starting from the left-hand side as shown in FIG. 2D. The actual number of T cells in blood is relatively small. Therefore, the distribution area of T cells coupled with the latex-labeled antibody is actually smaller than the area shown in this Figure. However, the area is enlarged for easy recognition in FIG. 2D. Distribution of the latex-labeled antibodies indicates extra latex-labeled antibodies which have not coupled with T cells. According to the biological microparticle inspection apparatus of the present invention, T cells can be correctly discriminated and counted at high speed, thereby aiding in correct diagnosis.

Figure 6:
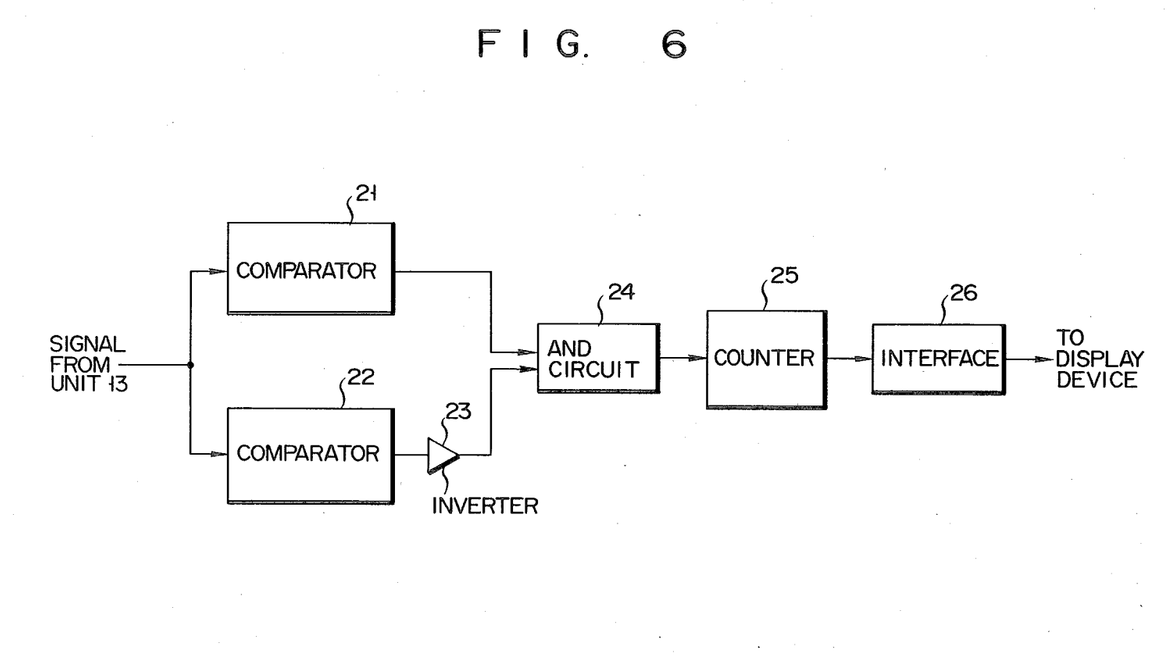
FIG. 6 is a block diagram of the signal processing unit used in the apparatus of the first embodiment.

FIG. 6 shows a block diagram of the signal processing unit 14. An electrical signal representing the electrical resistance or forward scattered light intensity measured by the unit 13 is supplied to comparators 21 and 22.

The comparator 21 is a logic circuit which comprises an IC that produces an output signal of logic level "1" upon reception of a pulse exceeding a threshold TH1, as shown in FIG. 2D. Similarly, the comparator 22 comprises a logic circuit which produces an output signal of logic level "1" upon reception of a pulse exceeding a threshold TH2. A signal from the comparator 22 is inverted by an inverter 23. Output from the inverter 23 and output from the comparator 21 are supplied to an AND circuit 24.

The AND circuit 24 produces an output signal which goes from "0" to "1" only when the input signals from the inverter 23 and the comparator 21 fall within the range between the thresholds TH1 and TH2. Thus, when the number of output signals of "1" from the AND circuit 24 is counted by the counter 25, the total indicates the number of pulses having magnitudes within the range between the thresholds TH1 and TH2, and, thus, the total number of the desired blood cells. The counted pulse number is supplied to the display device 15 through an interface 26.

In the first embodiment just described above, input signals are processed using two comparators. However, other processing can be performed. For example, peak of input signals can be held, the pulse magnitudes can be converted into digital values by an A/D converter, and the digital values can be processed by an operational unit such as a microcomputer.

Figure 3A:
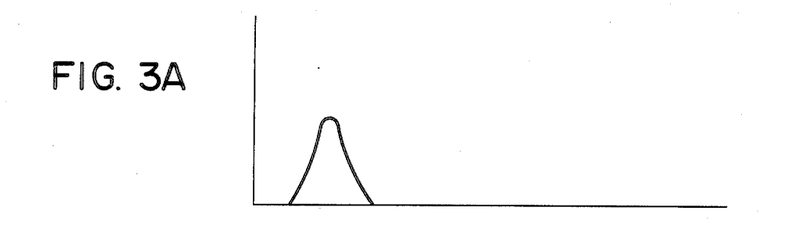
Figure 3B:
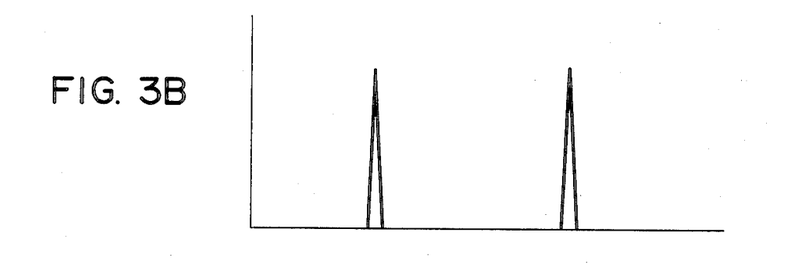
Figure 3C:
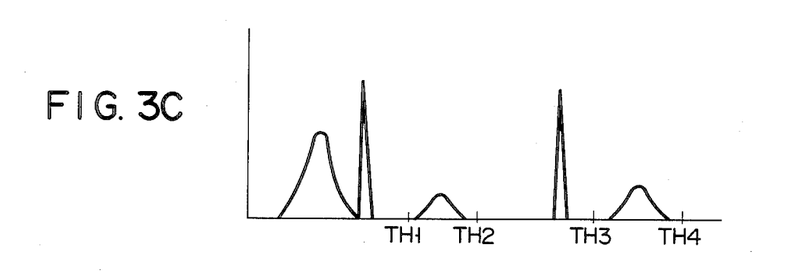

T and B cells in the same sample can be discriminated and counted separately. In this case, latex particles 19.8 $\mu$m in size are used for labeling T cells, and latex particles 44.1 $\mu$m in size are used for labeling B cells. FIG. 3A shows a histogram of a blood corpuscle sample, and FIG. 3B shows a histogram of a T cell-specific, latex-labeled antibody on the left and a histogram of a B cell-specific, latex-labeled antibody on the right. When the two latex-labeled antibodies are mixed with the blood 4 by the apparatus shown in FIG. 1 and the mixture is measured by the unit 13, the histogram shown in FIG. 3C is obtained. Referred to FIG. 3C, blood corpuscles with forward scattered light intensity or electrical resistance values measured between the thresholds TH1 and TH2 are discriminated from other sample particles and counted as T cells coupled to the T cell-specific, latex-labeled antibody. Blood corpuscles with forward scattered light intensity or electrical resistance values measured between the thresholds TH3 and TH4 are discriminated and counted as B cells coupled with the B cell-specific, latex-labeled antibody.

Although latex particles of 19.8 and 44.1 $\mu$m are used in this embodiment, latex particles of other particle sizes can be used. Note that when a sample is blood, latex particles of a particle size larger than that of the blood corpuscles are preferable for use. In practice, latex particles having a particle size 1/10 to ten times that of particles to be measured can be used.

Many types of particles can be simultaneously detected by using latex particles having different particle sizes. The signal processing unit 14 can be used to calculate the proportion of a certain type of corpuscle to the total number of blood corpuscles.

In the first embodiment, the particle size measurement unit 13 is used as an apparatus for measuring the size of particles by detecting the forward scattered light intensity or electrical resistance of the particles. In a second embodiment, to be described below, the particle size measurement unit 13 of the first embodiment is replaced with a forward/side scattered light measurement unit 16. The same reference numerals as in the first embodiment denote the same parts in the second embodiment shown in FIG. 4, and a detailed description thereof will be omitted. The unit 16 is used on the basis of the fact that intensity of light scattered by the irradiation of particles differs in accordance with the particle size and scattering direction.

The theory of scattered light intensity is described by Max Born Emil Wolf in "Principles of Optics", pp. 633 to 664, Pergamom Press, Oxford; by G. C. Salzman in The International Academy of Cytology, 19, 374–377 (1975); and by Akira Kanagawa in Kagakukogyo (Chemical Industry), 34, 71–77 (1970). According to their theories, with small particles, the side scattered light intensity is higher than the forward scattered light intensity, and this difference is greater than that which occurs with large particles. When small particles are attached to particles of a larger size than the wavelength of illuminating light, the side scattered light intensity is higher than that of particles to which small particles are not attached. Therefore, when the side scattered light intensity is monitored, particles with or without small particles attached thereto can be discriminated.

Figure 4:
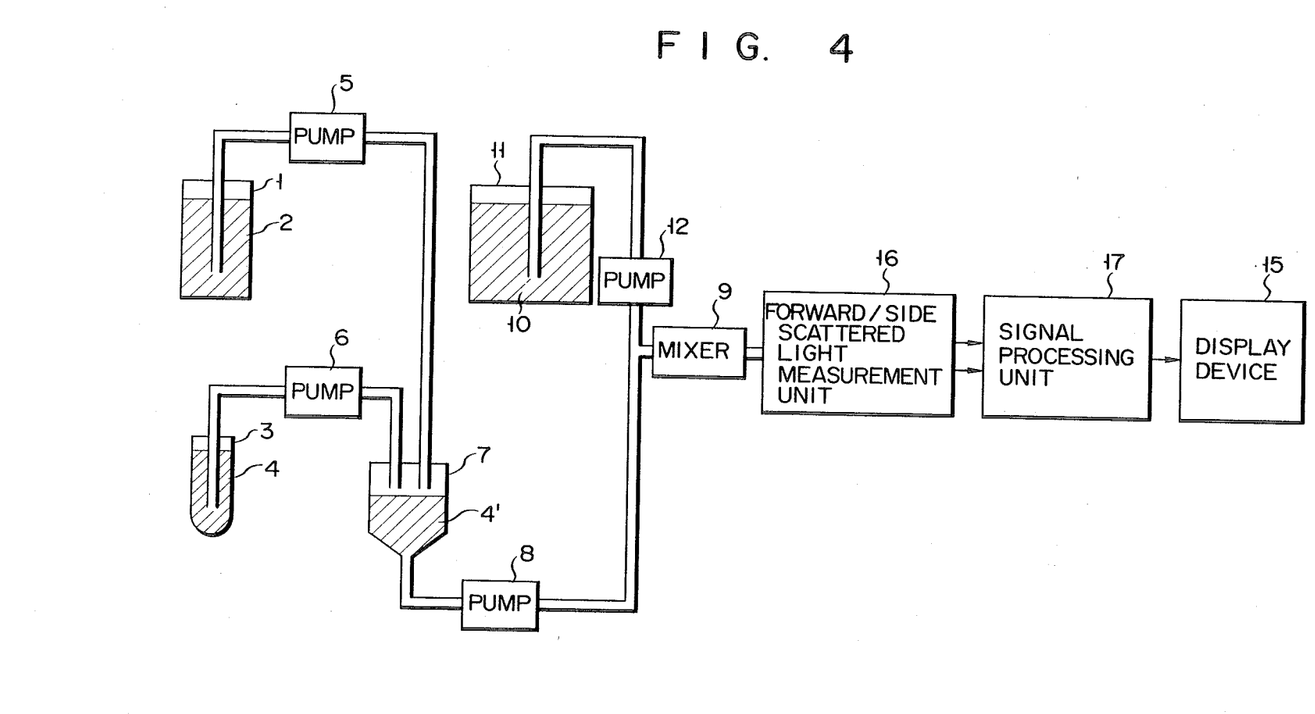
FIG. 4 shows a schematic configuration of the apparatus according to a second embodiment of the present invention.

The forward/side scattered light measurement unit 16 consists of a flow cell with an orifice of a transparent material such as glass, an optical system for illuminating a sample solution passing through the flow cell with light, and an optical system for receiving both the forward and side scattered light from the sample solution.

Figure 5A:
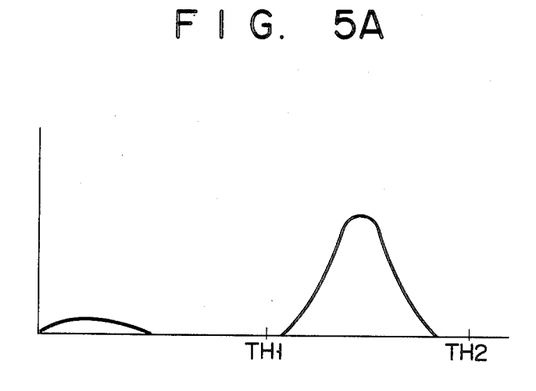
FIGS. 5A and 5B show histograms obtained in the second embodiment of the present invention.
Figure 5B:
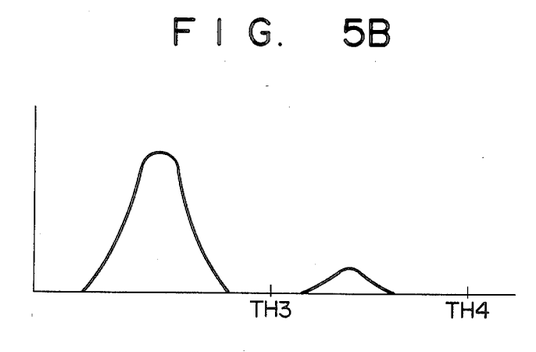

FIG. 5A shows histograms of the forward scattered light intensities of a latex-labeled antibody and T cells coupled therewith, measured by the unit 16. FIG. 5B shows histograms of the side scattered light intensities of a latex-labeled antibody and T cells coupled therewith. Referring to FIGS. 5A and 5B, as variables, the amount of scattered light from the particles is plotted along the abscissa axis, and the number of particles is plotted along the ordinate axis. The signal processing unit 17 selects particles having a forward scattered light intensity within the range between thresholds TH1 and TH2 as shown in FIG. 5A, and then counts, from among these particles, those having a side scattered light intensity within the range between thresholds TH3 and TH4. Thus, the T cells coupled with the latex-labeled antibody can be counted.

In the second embodiment, latex particles of 0.33 $\mu$m are used for labeling an antibody. However, when latex particles of other sizes are used, those about 1/10 the size of the particles to be counted are preferable. When the size of the latex particles is too large, the ratio of the side scattered to forward scattered light intensity becomes too small, and accurate measurement is impeded. Conversely, when the latex particle size is too small, the ratio of the side scattered to forward scattered light intensity can be high. In this case, the absolute values of the scattered light intensities become small, and accurate measurement is impeded once again.

Figure 7:
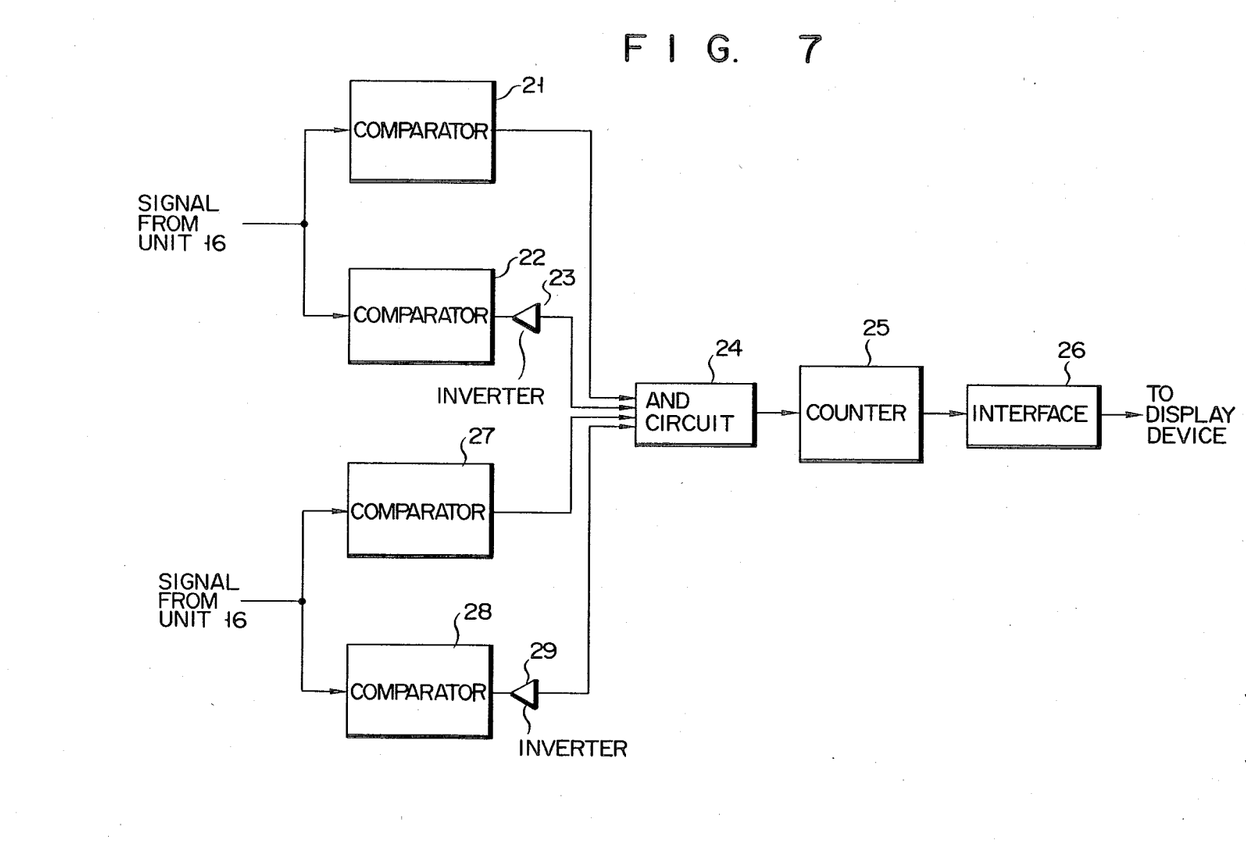
FIG. 7 is a block diagram of the signal processing unit used in the apparatus of the second embodiment.

FIG. 7 shows a block diagram of a signal processing unit 17. An electrical signal indicating forward scattered light detected by the unit 16 is supplied to comparators 21 and 22. The comparator 21 is a logic circuit, comprising an IC or the like, which produces an output signal of logic level "1" upon reception of a pulse exceeding the threshold TH1 shown in FIG. 5A. Similarly, the comparator 22 is a logic circuit which produces an output signal of logic level "1" upon reception of a pulse exceeding the threshold TH2. An output signal from the comparator 22 is inverted by an inverter 23. Output signal from the inverter 23 and output signal from the comparator 21 are supplied to an AND circuit 24.

An electrical signal indicating side scattered light detected by the unit 16 is supplied to comparators 27 and 28. The comparator 27 is a logic circuit such as an IC which produces an output signal of logic level "1" upon reception of a pulse exceeding the threshold TH3 as shown in FIG. 5B. Similarly, the comparator 28 is a logic circuit which produces an output signal of logic level "1" upon reception of a pulse exceeding the threshold TH4. An output signal from the comparator 28 is inverted by an inverter 29. Output signal from the inverter 29 and output signal from the comparator 27 are supplied to the AND circuit 24.

With this configuration, an output signal from the AND circuit 24 goes from logic level "0" to "1" when the input signals fall between the thresholds TH1 and TH2 and between the thresholds TH3 and TH4. Thus, when output signals of "1" from the AND circuit 24 are counted by a counter 25, only signals having pulse amplitudes between the thresholds TH1 and TH2 and between the thresholds TH3 and TH4 are counted. The count is supplied to a display device 15 through an interface 26.

In the second embodiment, input signals are processed using four comparators. However, other processing can be performed. For example, input signals can be peak-held, the pulse amplitudes can be converted into digital values by an A/D converter, and the digital values can be processed by an operational unit such as a microcomputer.

As described above, the same effect as that in the first embodiment can be obtained by using the forward/side scattered light measurement unit 16 of the second embodiment.

The present invention is not limited to the particular embodiments described above, and various other changes and modifications can be made within the spirit and scope of the present invention.

In the embodiments described above, blood is used as a sample. However, the sample can be phlegm, secretions of the uterine cervix, or the like. Similarly, though an antibody is used in the embodiments as a coupling body for labeling particles to be measured, a receptor can be used in its place. Finally, in the embodiments described above, in order to prevent simultaneous counting of two or more particles as a single particle, blood is diluted with a diluting solution at the mixer 9. However, if blood is diluted to a low concentration in advance, the diluting unit can be omitted. Moreover, a hemolyzing agent for breaking the cell membranes of erythrocytes can be used in place of a diluting solution.

What is claimed is:

1. A biological microparticle inspection apparatus comprising:

first means for mixing coupling bodies capable of coupling specifically with specified biological microparticles and labeled with particles having substantially the same size, together with a sample containing biological microparticles including said specified biological microparticles, thereby coupling said labeled coupling body with said specified biological microparticles to form complexes; and second means for selectively counting the number of said complexes, said second means comprising a particle size measurement unit for detecting the size of said complexes, and a signal processing unit for processing a signal from said particle size measurement unit and for counting the number of said complexes having a size falling within a predetermined size range.

2. An apparatus according to claim 1, wherein said particle size measurement unit comprises a flow cell with an orifice of a transparent material, through which a sample containing said complexes is allowed to pass; and a unit for irradiating the sample passing through said orifice with light and detecting forward scattered light from the sample.

3. An apparatus according to claim 1, wherein particle size measurement unit comprises a flow cell with an orifice of a transparent material such as glass, through which a sample containing said complexes is allowed to pass; and a unit for detecting, by electrodes before and after the sample passes through said orifice, a change in the electrical resistance of the sample passing through said orifice.

4. An apparatus according to claim 1, wherein said second means comprises a forward/side scattered light measurement unit for irradiating said complexes with light and detecting forward and side scattered light intensities; and a signal processing system for processing a signal from said forward/side scattered light measurement unit and for counting the number of said complexes corresponding, within a specific range, to the forward and side scattered light intensities.

5. An apparatus according to claim 1, wherein the coupling body is an antibody or a receptor which is specifically coupled to a specific type of biological microparticle.

6. An apparatus according to claim 1, wherein the particles for labeling the coupling body are synthetic resin particles having a uniform particle size.

7. An apparatus according to claim 1, wherein the particles for labeling the coupling body have different sizes in accordance with the type of biological microparticle to be measured.

8. An apparatus according to claim 1, wherein the labeled coupling body and the sample are diluted before being mixed together.

9. A method of detecting and counting specified biological microparticles, comprising:
    mixing coupling bodies capable of coupling specifically with specified biological microparticles and labeled with particles having substantially the same size, together with a sample containing biological microparticles including said specified biological microparticles, thereby coupling said labeled coupling body with said specified biological microparticles to form complexes; and
    selectively detecting and counting the number of said complexes.

10. A method according to claim 9, wherein said step of detecting and counting comprises:
    irradiating the mixture containing the complex with light to obtain forward and side scattered light,
    detecting intensities of the forward and side scattered light, and
    counting the number of the complexes in accordance with the intensities of the forward and side scattered light within a specific range.

* * * * *